United States Patent [19]

Oka et al.

[11] Patent Number: 5,001,278
[45] Date of Patent: Mar. 19, 1991

[54] NOVEL FLUOROVINYL ETHER AND COPOLYMER COMPRISING THE SAME

[75] Inventors: Masahiko Oka, Shiga; Yuji Yutani, Osaka; Masayasu Tomoda; Mitsuru Kishine, both of Shiga; Tetsuo Shimizu, Osaka, all of Japan

[73] Assignee: Daikin Industries, Ltd., Osaka, Japan

[21] Appl. No.: 177,822

[22] Filed: Mar. 24, 1988

Related U.S. Application Data

[63] Continuation of Ser. No. 844,593, Mar. 27, 1986, abandoned.

[30] Foreign Application Priority Data

Mar. 28, 1985 [JP] Japan ................................. 60-65185
Mar. 28, 1985 [JP] Japan ................................. 60-65186

[51] Int. Cl.$^5$ ................. C08F 12/20; C07C 41/00
[52] U.S. Cl. ........................... 568/615; 568/614; 568/684; 568/685; 526/242; 526/243; 526/245
[58] Field of Search ............... 526/242, 243, 245; 568/684, 685, 614, 615

[56] References Cited

U.S. PATENT DOCUMENTS 3,450,684  6/1969  Darby ................. 568/685
4,275,226  6/1981  Yamabe et al. ....... 568/685
4,513,128  4/1985  Uschold ............... 526/247

Primary Examiner—Peter F. Kulkosky
Attorney, Agent, or Firm—Birch, Stewart, Kolasch & Birch

[57] ABSTRACT

A fluorovinyl ether of the formula:

$$XCH_2CF_2CF_2-(OCH_2CF_2CF_2)_m-(OCFYCF_2)_n-OCF=CF_2 \qquad (I)$$

wherein X is a hydrogen atom or a halogen atom (e.g. fluorine, chlorine, bromine and iodine); Y is a fluorine atom or a trifluoromethyl group; m is an integer of 0 to 5; and n is 0, 1 or 2, which can modify a polymer of at least one ethylenically unsaturated compound.

6 Claims, No Drawings

NOVEL FLUOROVINYL ETHER AND COPOLYMER COMPRISING THE SAME

This application is a continuation of application Ser. No. 844,593 filed on Mar. 27, 1986, now abandoned.

FIELD OF THE INVENTION

The present invention relates to a novel fluorovinyl ether and a copolymer comprising the same. More particularly, it relates to a novel fluorovinyl ether useful as a modifier of a polymer comprising an ethylenically unsaturated compound, and a copolymer comprising at least one ethylenically unsaturated compound and the novel fluorovinyl ether.

BACKGROUND OF THE INVENTION

Copolymerization of a fluoroolefin with other fluoroolefins or non-fluoroolefins provides a copolymer having a wide range of properties from a resin to an elastomer depending on the kinds and/or contents of the fluoroolefin and other monomers. Therefore, the copolymer of the fluoroolefin has various applications, for example, as a part such as an O-ring, a flange seal, a gasket, a diaphragm and a liner and is particularly useful in a field in which excellent resistance to heat and/or corrosion is required.

For producing an elastomeric polymer, a cross linking method plays an important role. Since a copolymer of the fluoroolefin is thermally and chemically stable, it is difficult to cross-link it. For cross-linking the copolymer of fluoroolefin, it has been proposed to copolymerize a monomer which provides a cross-linking site to the polymer. As the monomer providing the cross-linking site, there have been proposed an unsaturated compound having a perfluorophenoxy group (cf. Japanese Patent Publication No. 11823/1972), a nitro group (Japanese Patent Publication No. 26303/1970 and Japanese Patent Kokai Publication (unexamined) No. 61119/1974) or a bromine atom (Japanese Patent Publication Nos. 4115/1978 and 1585/1979). However, it takes longer time to cross-link the copolymer containing such monomer, and the cross-linked product has still unsatisfactory physical properties.

Among the resinous polymers of the fluoroolefins, polytetrafluoroethylene (hereinafter referred to as "PTFE") is most widely used and molded to form various articles. Conventionally, PTFE having a molecular weight of 1,000,000 or more is used for molding. However, since PTFE having such high molecular weight has a large melt viscosity, for example, of $1 \times 10^8$ PaS at 380° C., its melt processing is very difficult. To decrease the melt viscosity of PTFE, some copolymers of tetrafluoroethylene and other fluorine-containing monomers are proposed and commercially available. These copolymers which contain other monomers in an amount not larger than 2% by mole are called modified PTFE and are processed by substantially the same molding method as PTFE. Examples of the monomer are $CF_3CF=CF_2$, $C_3F_7OCF=CF_2$, $ClCF=CF_2$, $C_4F_9CH=CH_2$ and mixtures thereof. It is still highly desirable to provide a modified PTFE having further improved performances in molding in comparison with pure PTFE.

SUMMARY OF THE INVENTION

One object of the present invention is to provide a novel fluorovinyl ether which can provide a cross-linking site to a polymer of an ethylenically unsaturated compound, particularly a fluorine-containing ethylenically unsaturated compound.

Another object of the present invention is to provide an elastomeric polymer comprising an ethylenically unsaturated compound which can be cross-linked in a shorter period of time.

A further object of the present invention is to provide an elastomeric polymer comprising an ethylenically unsaturated compound a cross-linked product of which has good physical properties such as tensile strength, elongation, heat resistance and compression set.

Yet another object of the present invention is to provide an elastomeric polymer having improved low temperature properties.

Yet a further object of the present invention is to provide a modified PTFE of a granule form which is molded by compression molding and ram injection molding to provide an article having improved creep resistance after sintering.

Still another object of the present invention is to provide a modified PTFE of a fine powder form which can be molded by paste extrusion to provide an article having considerably improved mechanical strength before sintering.

These and other objects are accomplished by forming a fluorovinyl ether of the formula:

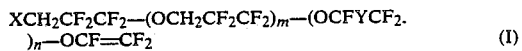

wherein X is a hydrogen atom or a halogen atom (e.g. fluorine, chlorine, bromine and iodine); Y is a fluorine atom or a trifluoromethyl group; m is an integer of 0 to 5; and n is 0, 1 or 2, and a copolymer comprising at least one ethylenically unsaturated compound and the fluorovinyl ether (I).

DETAILED DESCRIPTION OF THE INVENTION

The fluorovinyl ether (I) may be derived from a corresponding acyl fluoride which is prepared by a method described in U.S. patent application Ser. No. 684,344 and European patent application No. 84 116 103.7 (EP-A-No. 0148490) or U.S. patent application Ser. No. 684,345 and European patent application No. 84 116 003.9 (EP-A-No. 0148482), the disclosures of which are hereby incorporated by reference.

When Y in the formula (I) is a trifluoromethyl group, a corresponding acyl fluoride is converted to the fluorovinyl ether as follows:

An acyl fluoride of the formula:

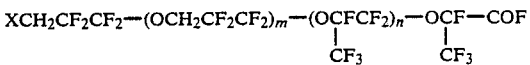

is reacted with a lower alcohol such as methanol to form an ester of the formula:

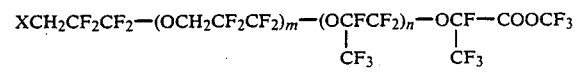

The resulting ester is then reacted with an alkali metal hydroxide (MOH) such as sodium hydroxide to form a salt of the formula:

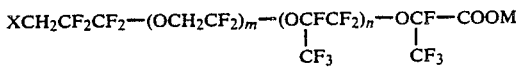

The salt is heated at a temperature of 150° to 250° C. in a stream of an inert gas such as nitrogen or under reduced pressure to form the fluorovinyl ether (I).

The ethylenically unsaturated compound which is copolymerized with the fluorovinyl ether (I) may be any conventional compound. Specific examples of the ethylenically unsaturated compound are fluorine-not-containing ethylenically unsaturated compound (e.g. ethylene, propylene, butylene, vinyl carboxylate such as vinyl acetate, vinyl ether such as methyl vinyl ether and ethyl vinyl ether, vinyl chloride, vinylidene chloride, acrylic acid and methacrylic acid), and fluorine-containing ethylenically unsaturated compounds (e.g. tetrafluoroethylene, trifluoroethylene, chlorotrifluoroethylene, vinyl fluoride, vinylidene fluoride, hexafluoropropylene, pentafluoropropylene, hexafluoroisobutene, perfluorocyclobutene, perfluoro(methylcyclopropylene), perfluoroallene, $\alpha,\beta,\beta$-trifluorostyrene, perfluorostyrene, perfluoroalkyl vinyl ether such as perfluoro(methyl vinyl ether) and perfluoro(propyl vinyl ether), perfluoro(alkyl vinyl polyether), polyfluoroacrylic acid, polyfluorovinyl acetate, polyfluorovinyl ether sulfonate and polyfluorodienes).

The amount of the fluorovinyl ether (I) in the copolymer depends on the kind of the copolymer to be produced. In general, it is from 0.01 to 60% by mole based on the total molar content of other monomer(s). To provide cross-linking sites to the elastomeric copolymer, the amount of the fluorovinyl ether (I) is from 0.01 to 5% by mole, preferably from 0.1 to 5% by molar content based on the mole of other monomer(s). To improve the low temperature properties of the elastomeric copolymer, it is from 5 to 60% by mole, preferably from 10 to 50% by molar content based on the mole of other monomer(s). To modify the resinous polymer such as PTFE, it is from 0.01 to 2% by mole, preferably from 0.03 to 1% by mole based on the mole of other monomer(s).

According to the first preferred embodiment of the present invention, an elastomeric copolymer comprises 50 to 95% by mole of repeating units derived from a fluoroolefin of the formula:

wherein A and B are, the same or different, each a fluorine atom or a chlorine atom, 50 to 5 % by mole of repeating units derived from a perfluorovinyl ether of the formula:

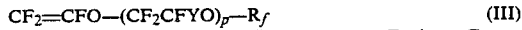

wherein Y is the same as defined above, $R_f$ is a $C_1$-$C_6$ fluoroalkyl group, and p is an integer of 0 to 5 and repeating units derived from the perfluorovinyl ether (I) of the invention in an amount of 0.1 to 5% by mole based on the total molar content of the fluoroolefin (II) and the perfluorovinyl ether (III). The terpolymer according to this embodiment may further comprise at least one other ethylenically unsaturated compound as described above. The amount of other ethylenically unsaturated compounds may be 0.1 to 20% by molar content based on the total mole of the above three compounds (I), (II) and (III).

According to the second preferred embodiment of the present invention, a copolymer comprises 20 to 90% by mole of repeating units derived from vinylidene fluoride, 10 to 80% by mole of repeating units derived from at least one ethylenically unsaturated compound except vinylidene fluoride and repeating units derived from the fluorovinyl ether (I) of the invention in an amount of 0.01 to 3% by mole based on the total molar content of vinylidene fluoride and other ethylenically unsaturated compounds. As the other ethylenically unsaturated compound, a mixture of 10 to 45% by mole of hexafluoropropylene and 0 to 35% by mole of tetrafluoroethylene is preferably used.

According to the third preferred embodiment of the present invention, a copolymer comprises 20 to 100% by mole of repeating units derived from vinylidene fluoride, 80 to 0% by mole of repeating units derived from at least one ethylenically unsaturated compound except vinylidene fluoride and repeating units derived from the fluorovinyl ether (I) of the invention in an amount of 5 to 60% by mole, preferably 10 to 50% by molar content based on the total mole of vinylidene fluoride and the other ethylenically unsaturated compound.

According to the fourth preferred embodiment of the present invention, a copolymer comprises repeating units derived from tetrafluoroethylene and repeating units derived from the fluorovinyl ether (I) of the invention in an amount of 0.01 to 2% by mole, preferably from 0.03 to 1% by mole based on the molar content of tetrafluoroethylene.

The elastomeric copolymer of the invention may be prepared by a per se conventional method which is employed to polymerize the conventional ethylenically unsaturated compound to produce an elastomeric copolymer. For example, the monomers are copolymerized by emulsion polymerization in the presence of a perfluoroemulsifier and a water- or oil-soluble peroxide, although they may be polymerized by bulk, suspension or solution polymerization.

In the solvent or emulsion polymerization, preferably used is a highly fluorinated solvent (e.g. dichlorodifluoromethane, trichlorofluoromethane, chlorodifluorohexafluoromethane 1,1,2-trichlroro-1,2,2-trifluoroethane, 1,2-dichloro-1,1,2,2-tetrafluoroethane, 1,1,2,2-tetrachloro-1,2difluoroethane, perfluorocyclobutane and perfluorodimethylcyclobutane).

Polymerization is usually initiated with an organic polymerization initiator. Preferred examples of the polymerization initiators are highly fluorinated peroxides, particularly a diacylperoxide of the formula:

wherein $R_f'$ is a perfluoroalkyl group, a $\omega$-hydroperfluoroalkyl group or a perchlorofluoroalkyl group.

The polymerization temperature depends on the decomposition temperature of the polymerization initiator and is preferably from 0° to 130° C.

The polymerization pressure may be from 5 to 50 kg/cm²G.

The molecular weight of the elastomeric copolymer of the invention can be easily controlled by the addition of a chain transfer agent. Specific examples of the chain transfer agent are a $C_4$-$C_6$ hydrocarbon, an alcohol, an ether and a halogen-containing organic compound (e.g. $CCl_4$, $CBrCl_3$, $CF_2BrCFBrCF_3$ and $CF_2I_2$). When an iodine-containing fluorocarbon (e.g. $CF_2I_2$, $I(CF_2)_4I$ and $CF_2=CFCF_2CF_2I$) is used as the chain transfer agent, an iodine atom is bonded at a chain end of the copolymer and still radically active. Therefore, the copolymer can be advantageously cross-linked with peroxide as a radical source in the presence of a polyfunctional unsaturated compound (e.g. triallylisocyanurate and triallylcyanurate).

In general, the elastomeric copolymer of the invention can be cured in the presence of at least one cross-linking source. A preferred example of the cross-linking source is an organic peroxide, although radioactive rays (e.g. alpha-rays, beta-rays, gamma-rays and X-rays) and a high energy electromagnetic wave (e.g. ultraviolet light) may be used as the cross-linking source.

When the organic peroxide is used as the cross-linking source, it is used in an amount of 0.05 to 10 parts by weight, preferably 1.0 to 5 parts by weight per 100 parts by weight of the copolymer.

The organic peroxide includes those that easily generate a peroxy radial in the presence of heat energy or an oxidation-reduction system. Its particular examples are 1,1-bis(t-butylperoxy)-3,5,5-trimethylcyclohexane, 2,5-dimethylhexane2,5-dihydroperoxide, di-t-butylperoxide, t-butylcumylperoxide, dicumylperoxide, $\alpha,\alpha'$-bis(t-butylperoxy)-p-diisopropylbenzene, 2,5-dimethyl-2,5-di(t-butylperoxy)hexane, 2,5-dimethyl-2,5-(t-butylperoxy)hexine-3, benzoylperoxide, t-butylperoxybenzene, 2,5-diemthyl-2,5-di(benzoylperoxy)hexane, t-butylperoxymaleic acid, t-butyl peroxyisopropyl carbonate and the like. Among them, the dialkyl type peroxides are preferred. The amount and kind of the peroxide are selected according to the amount of active—O—O— groups and cross-linking conditions such as a decomposition temperature of the peroxide.

When the organic peroxide compound is used as the cross linking source, cross-linking is facilitated by the addition of a cross-linking coagent. As the cross-linking coagent, any of conventional ones may be used insofar as it is reactive with the peroxy radical and the polymer radical. Their preferred examples are triallylcyanurate, triallylisocyanurate, triacrylformal, triallyltrimeritate, N,N'-m-phenylenebismaleimide, dipropargyl terephthalate, diallyl phthalate, tetrallyl teraphthalamide, trially phosphate and the like. The amount of the cross-linking coagent is from 0.1 to 10 parts by weight, preferably from 0.5 to 5 parts by weight per 100 parts by weight of the copolymer to be cross-linked.

The copolymer of the invention may be blended and cocross-linked with at least one other polymer. Examples of such cocross-linkable other polymers are silicone oil, silicone rubber, ethylene-vinyl acetate copolymer, poly-1,2-butadiene, fluorosilicone oil, fluorosilicone rubber, fulorophosphazene rubber, hexafluoropropylene-ethylene copolymer, tetrafluoroethylene-propylene copolymer and the like. Further, a polymer having radical reactivity may be blended and cocross-linked with the copolymer of the invention. The amount of the blended polymer may be such amount that the characteristic properties of the copolymer of the invention are not deteriorated.

The elastomeric copolymer of the invention may contain a pigment for coloring the product, a filler or a reinforcing material. Usually used filler or reinforcing material includes, as an inorganic material, carbon black, titanium oxide ($TiO_2$), silica, clay and talc, and as an organic material, fluorine-containing polymers (e.g. polytetrafluoroethylene, polyvinylidene fluoride, polyvinyl fluoride, polychlorotrifluoroethylene, tetrafluoroethylene-ethylene copolymer and tetrafluoroethylene-vinylidene fluoride copolymer).

The curing component may be blended in the copolymer of the invention by a suitable method depending on the viscoelasticity and form of the materials to be blended. The powder materials are mixed by means of open rolls or a powder mixer, while the liquid materials are mixed by means of a conventional mixer. Further, the solid materials may be dispersed or dissolved in a solvent and mixed.

The cross-linking conditions depend on the kind of the peroxide. In general, press cure is carried out at a temperature of 120° to 200° C. for 5 to 30 minutes, and oven cure is carried out at a temperature of 150° to 250° C. for 1 to 24 hours.

The elastomeric copolymer of the present invention can be used as a molding material, a sealant, an adhesive or a coating in various fields in which a polymeric material is required to have good chemical resistance, thermal resistance, oil resistance and/or solvent resistance.

The resinous copolymer of the invention, particularly the modified PTFE may be produced by suspension polymerization followed by finely grinding (a granular type resin) or emulsion polymerization followed by coagulation of latex (a fine powder type resin). The polymerization procedure may be the same as used for produce PTFE or conventional modified PTFE. For example, the suspension polymerization is described in Japanese Patent Publication Nos. 25398/1976 and 31524/1984, and the emulsion polymerization is described in U.S. Pat. No. 2,965,595. Generally, modified PTFE of the invention is produced as follows:

In a temperature-controllable reaction vessel equipped with a stirrer, deionized deoxidized water and various additives are added and replaced with nitrogen gas several times. After the vessel is pressurized with tetrafluoroethylene, the fluorovinyl ether (I) and the polymerization initiator are added. The reaction pressure is usually kept at 4 to 30 kg/cm$^2$G by the injection of tetrafluoroethylene. The reaction temperature is kept from 10° to 120° C. In the suspension polymerization, the reaction mixture is vigorously stirred to disperse the produced powdery polymer, while in the emulsion polymerization, it is gently stirred to stabilize the formed latex. To improve the stability of the latex, a hydrocarbon having 12 or more carbon atoms which is inert to the polymerization reaction may be added to the emulsion polymerization system. Examples of the additives are a buffer, a molecular weight regulating agent (a chain transfer agent), a polymerization initiating aid, a non-tackifier, a fluorine-containing dispersing agent (a surfactant) and the like. The major difference between the suspension polymerization and the emulsion polymerization resides in that the former utilized little or no dispersing agent, while the latter used the dispersing agent in such an amount as to stabilize the latex particles, for example, about 100 to 10,000 ppm.

Modified PTFE of the invention has superior properties to non-modified PTFE. For example, granular type modified PTFE of the invention can be molded by compression molding or ram injection molding and a sintered molded article has improved creep resistance. The fine powder of the modified PTFE can be molded by past extrusion and an unsintered molded article has better mechanical strength.

The copolymer of the present invention comprising the fluorovinyl ether (I) is a highly reactive polymer since it contains side chains having reactive halogen atoms (e.g. iodine, bromine and chlorine). The reactive halogen atoms may be converted to other functional groups such as hydrophilic groups (e.g. hydroxyl groups, carboxyl groups and sulfonic acid groups) by per se conventional methods. The copolymer having the hydrophilic groups in the side chains may be used as an ion exchange resin with good heat and chemical resistance. Further, it may be used as a separating, filtrating or sieving hydrophilic film, or a biomaterial.

The present invention will be explained further in detail by following examples, wherein parts are by weight unless otherwise indicated.

PREPARATION OF ACYL FLUORIDE

Reference Example 1

2,2,3-Trifluoropropionyl fluoride

In a 5 liter flask equipped with a stirrer, a condenser and a dropping funnel, carbon tetrachloride (360 ml) and aluminum chloride (108 g) were charged and kept at a temperature of 30° to 35° C. Then, 2,2,3,3-tetrafluorooxetane (hereinafter referred to as "tetrafluorooxetane") (1,800 g) was dropwise added over 2 hours with stirring. To complete the reaction, three portions of aluminum chloride (each 30 g) were added every 1.5 hours. Then, the reaction was continued at a temperature of 27° to 29° C. for 4 hours. The reaction mixture was distilled to give the entitled compound (1,130 g). B.P. 23°-23.5° C.

Reference Example 2

2,2,5,5,6,6,7-Heptafluoro-4-oxa-heptanoyl fluoride and 2,2,5,5,6,6,9,9,10,10-decafluoro-4,8-dioxa-undecanoyl fluoride In the same flask as used in Reference Example 1, 2,2,3-trifluoropropionyl fluoride (1,059 g), crown ether (5 g), cesium fluoride (40 g) and monoglyme (1,000 ml) were charged. Then, tetrafluorooxetane (1,515 g) was dropwise added with stirring at a temperature of 15° to 20° C. over 3.5 hours. Thereafter, the reaction was continued with stirring at a temperature of 15° to 20° C. for 5 hours. The reaction mixture was distilled under reduced pressure to give 2,2,5,5,6,6,7-heptafluoro-4-oxa-heptanoyl fluoride (300 g. B.P. 62°-64° C./80 mmHg) and 2,2,5,5,6,6,9,9,10,10-decafluoro-4,8-dioxa-undecanoyl fluoride (264 g. B.P. 23° C./5 mmHg).

Reference Example 3

2,2-Difluoro-3-iodopropionyl fluoride

In a four necked 3 liter flask, dry tetraglyme (1,500 ml) was charged and then sodium iodide (825 g) was completely dissolved therein. Thereafter, tetrafluorooxetane (650 g) was dropwise added at a temperature of 30° to 40° C. over 45 minutes. The reaction mixture was distilled at a temperature of 38° to 40° C. under a reduced pressure of 30 mmHg to yield the entitled compound (1,050 g). B.P. 95°-96° C.

PREPARATION OF THE FLUOROVINYL ETHER (I)

Example 1

Perfluoro(6,6-dihydro-3-oxa-1-hexene)

(FCH$_2$CF$_2$CF$_2$OCF=CF$_2$)

(a) In a four necked 3 liter flask containing cesium fluoride (88 g) and tetraglyme (34 ml), 2,2,3-trifluoropropionyl fluoride prepared in Reference Example 1 (1,055 g) was added. Then, hexafluoropropylene (hereinafter referred to as "HFPO") was injected at a temperature of −10° to −15° C. at such a rate that the reaction mixture was refluxed by a dry ice cooled condenser. After 52 hours from the initiation of the reaction, the injection of HFPO was terminated and methanol (1,324 ml) was added with cooling by ice water. The reaction mixture was washed with water several times and distilled to give a compound (804 g) of the formula:

FCH$_2$CF$_2$CF$_2$OCF(CF$_3$)COOCH$_3$     (1)

B.P. 38° C.

(b) The methyl ester (1) prepared in the previous step (a) was charged in 2 liter flask and saponified with a 10% by weight solution of sodium hydroxide in methanol at a temperature of 60° to 70° C. while using phenolphthalein as a pH indicator. From a resulting slightly pink colored viscous solution, methanol was distilled off under reduced pressure and the residue was dried under reduced pressure until a constant weight was reached to give a solid material (810 g).

To a 3 liter flask connected with a dry ice cooled trap, the ground solid material was added and replaced with nitrogen gas. Then, the flask was heated from 150° C. to 250° C. in a stream of nitrogen over 5 hours. The trap contained a liquid, which was distilled to give the entitled compound (324 g). B.P. 61°-62° C.

Example 2

Perfluoro(6,6,10,10-tetrahydro-3,7-dioxa-1-decene)

(FCH$_2$CF$_2$CF$_2$OCH$_2$CF$_2$CF$_2$OCF=CF$_2$)

In the same manner as in Example 1 but using FCH$_2$CF$_2$CF$_2$OCH$_2$CF$_2$OCF (204 g) prepared in Reference Example 2, the reactions were carried out to give the entitled compound (65 g). B.P. 44°-45° C./13 mmHg.

Example 3

Perfluoro(6,6,10,10,14,14-hexahydro-3,7,11-trioxa1-tetradecene)

(FCH$_2$CF$_2$CF$_2$OCH$_2$CF$_2$CF$_2$OCH$_2$CF$_2$C-F$_2$OCF=CF$_2$)

In the same manner as in Example 1 but using FCH$_2$CF$_2$CF$_2$OCH$_2$CF$_2$CF$_2$OCH$_2$CF$_2$COF (321 g) prepared in Reference Example 3, the reactions were carried out to give the entitled compound (54 g). B.P. 88°-89° C./13 mmHg.

Example 4

Perfluoro(6,6-dihydro-6-iodo-3-oxa-1-hexene (ICH$_2$CF$_2$CF$_2$OCF=CF$_2$)

(a) In a four necked 2 liter flask, cesium fluoride (43 g), tetraglyme (6 ml) and 2,2-difluoro-3-iodopropionyl fluoride prepared in Reference Example 4 (400 g) were charged. Then, HFPO was injected at 10° C. at such a rate that the reaction mixture was refluxed by a dry ice cooled condenser. After 21 hours from the initiation of the reaction, the injection of HFPO was terminated and methanol (300 ml) was added while cooling by ice water. The reaction mixture was washed with water several times and distilled to give a compound (205 g) of the formula:

ICH$_2$CF$_2$CF$_2$OCF(CF$_3$)COOCH$_3$     (2)

B.P. 114°–115° C./100 mmHg.

(b) The methyl ester (2) prepared in the previous step (a) was charged in 1 liter flask and saponified with a 10% by weight solution of sodium hydroxide in methanol at a temperature of 60° to 70° C. while using phenolphthalein as a pH indicator. From a resulting solution, methanol was distilled off and the residue was dried under reduced pressure until a constant weight was reached to give a slightly pinkish white solid material (202 g).

To a 1 liter flask connected with a dry ice cooled trap, the ground solid material was added and replaced with nitrogen gas. Then, the flask was heated from 150° to 250° C. under reduced pressure of 25 mmHg over 3 hours. The trap contained a purple liquid (148 g), which was distilled to give the entitled compound (81 g). B.P. 71°–72° C./100 mmHg.

Example 5

Perfluoro(9,9-dihydro-9-iodo-5-trifluoromethyl3,6-dioxa-1-nonene $(ICH_2CF_2CF_2OCF(CF_3)CF_2OCF=CF_2)$ (a) In a four necked 2 liter flask, cesium fluoride (60 g), tetraglyme (10 ml) and 2,2-difluoro-3-iodopropionyl fluoride prepared in Reference Example 4 (600 g) was added. Then, HFPO was injected at 10° C. at such a rate that the reaction mixture was refluxed by a dry ice cooled condenser. After 30 hours from the initiation of the reaction, the injection of HFPO was terminated and methanol (500 ml) was added while cooling by ice water. The reaction mixture was washed with water several times and distilled to give a compound (116 g) of the formula:

$$ICH_2CF_2CF_2OCF(CF_3)CF_2OCF(CF_3)COOCH_3 \quad (3)$$

B.P. 91°–92° C./6 mmHg.

(b) The methyl ester (3) prepared in the previous step (a) was thermally decomposed in the same manner as in Example 3, step (b) to give the entitled compound (63.5 g). B.P. 87°–87.5° C./45 mmHg.

PREPARATION OF COPOLYMERS

Example 6

In a glass-lined 3 liter autoclave containing pure water 1,660 ml cooled at 5° C., a compound of the formula:

$$C_3F_7-(OCF(CF_3)CF_2)_2OCF=CF_2$$

(hereinafter referred to as $\phi_2VE$) (300 g), a compound of the formula:

$$ICH_2CF_2CF_2OCF=CF_2$$

(7.6 g) as a monomer for providing a cross-linking site, $C_7F_{15}COONH_4$ (15 g) and a solution of 1,3,5-trichloroperfluorohexanoyl peroxide in 1,1,2-trichloro-1,2,2-trifluoroethane (concentration, 0.44 g/ml) (9.6 ml) were charged and an interior atmosphere was quickly replaced with tetrafluoroethylene repeatedly. Then, tetrafluoroethylene was injected at 5° C. to pressurize to 2.2 kg/cm²G.

As the reaction proceeded, the pressure dropped. When the pressure dropped to 2.0 kg/cm²G, tetrafluoroethylene was injected to repressurize to 2.2 kg/cm²G. With a repeating decrease and increase of pressure, the polymerization was continued for 28 hours and 40 minutes.

After the polymerization was completed, the unreacted monomers were purged and then the polymerization product was recovered, washed with water and dried to give a copolymer containing 28% by mole of $\phi_2VE$ (182 g). Iodometry of the copolymer revealed that the copolymer contained 0.69% by mole of $ICH_2CF_2CF_2OCF=CF_2$.

Examples 7 to 10

In the same manner as in Example 6 but using a solution of 1,3,5-trichloroperfluorohexanoyl peroxide (DLP) in 1,1,2-trichloro-1,2,2-trifluoroethane (0.44 g/ml) and the following fluorovinyl ether of the invention in amounts shown in Table 1, the polymerization was carried out under a reaction pressure for a period of time as shown in Table 1 to give a polymer:
(Examples 7 to 9)
$ICH_2CF_2CF_2OCF=CF_2$
(Example 10)
$ICH_2CF_2CF_2OCF(CF_3)CF_2OCF=CF_2$.

Yield and the contents of the fluorovinyl ether of the invention and $\phi_2VE$ are shown in Table 1.

TABLE 1

| Example No. | 7 | 8 | 9 | 10 |
|---|---|---|---|---|
| Conditions |  |  |  |  |
| Reaction pressure (kg/cm² G) | 1.8–2.2 | 1.6–2.2 | 1.8–2.2 | 1.8–2.2 |
| Reaction time | 30 hr | 42 hr 10 min | 41 hr | 28 hr |
| DLP (ml) | 5.3 | 5.3 | 2.6 | 9.6 |
| Fluorovinyl ether (g) | 4.4 | 2.96 | 4.45 | 11.3 |
| Results |  |  |  |  |
| Yield (g) | 125.3 | 150.7 | 98.8 | 173 |
| Content of fluorovinyl ether (mole %) | 0.58 | 0.32 | 0.76 | 0.75 |
| Content of $\phi_2VE$ (mole %) | — | 26 | — | 29 |

To the copolymer prepared in one of Examples 6 to 10, the components as shown in Table 2 were added to prepare by a curastometer (JSR II type). The composition was press cured at 160° C. for 10 minutes and oven cured at 180° C. for 4 hours and the physical properties of the cured composition were measured according to JIS K 6301. The results are shown in Table 2.

TABLE 2

| Example No. | 6 | 7 | 8 | 9 | 10 | Comp. 1 |
|---|---|---|---|---|---|---|
| Copolymer (parts) | 100 | 100 | 100 | 100 | 100 | 100 |
| MT-carbon (parts) | 10 | 10 | 10 | 20 | 10 | 1 |
| Triallylisocyanurate (parts) | 4.0 | 4.0 | 4.0 | 3.0 | 4.0 | 4.0 |
| Perhexa-2,5B (parts) | 1.5 | 1.5 | 1.5 | 1.0 | 1.5 | 1.5 |
| $v_{min}$ (kg) | 0.03 | 0.01 | 0.01 | 0.04 | 0.03 | 0.04 |
| $v$ (kg) | 3.45 | 1.14 | 1.5 | 2.55 | 3.65 | No |
| $T_{10}$ (min.) | 1.1 | 1.1 | 1.0 | 0.9 | 1.1 | increase |
| $T_{90}$ (min.) | 5.7 | 3.7 | 3.8 | 2.4 | 5.0 | of |
| R (min.) | 4.6 | 2.6 | 2.8 | 1.5 | 3.9 | torque |
| $M_{100}$ (kg/cm²) | — | 39 | 31 | 74 | 85 | No |
| $T_B$ (kg/cm²) | 93 | 60 | 45 | 80 | 98 | sheet |
| $E_B$ (%) | 83 | 185 | 160 | 106 | 110 | could |
| Hardness (JIS, Hs) | 70 | 65 | 63 | 83 | 73 | be formed |

Example 11

In a 3 l reaction vessel, pure water (1 liter) and, as an emulsifier, $C_7F_{15}COONH_4$ (2 g) were charged. After replacing the interior atmosphere with nitrogen gas, $ICH_2CF_2CF_2OCF=CF_2$ (2.5 g) were injected and then, at 80° C., a mixture of vinylidene fluoride (VdF), hexafluoropropylene (HFP) and tetrafluoroethylene (TFE) in a molar ratio of 18:71:11 was injected to pressurize the interior to 16 kg/cm$^2$G. Thereafter, a solution of ammonium persulfate (3.3 g) in pure water (80 ml) was injected together with nitrogen gas to initiate polymerization.

As the reaction proceeded, the pressure dropped. When the pressure dropped to 14 kg/cm$^2$G, a mixture of VdF, HFP and TFE in a molar ratio of 50:30:20 was injected to repressurize to 16 kg/cm$^2$G. With a repeating decrease and increase of pressure, the polymerization was continued for 8 hours and 45 minutes while injecting $ICH_2CF_2CF_2OCF=CF_2$ (each 2.5 g) after 1.7, 3.6 and 7.1 hours from the initiation of polymerization.

After cooling the reaction vessel, the unreacted monomers were purged to give an aqueous emulsion with a solid content of 25.7% by weight.

To the emulsion, a 5% aqueous solution of potassium alum was added to coagulate the product. The coagulated product was washed with water and dried to give an elastomeric copolymer (347 g). Mooney viscosity (100° C.), 32. According to iodometry, the copolymer contained 0.76% by mole of $ICH_2CF_2CF_2OCF=CF_2$.

Example 12

In a 3 l reaction vessel, pure water (1 liter) and, as an emulsifier, $C_7F_{15}COONH_4$ (2 g) were charged. After replacing the interior atmosphere with nitrogen gas, a mixture of VdF, HFP and TFE in a molar ratio of 18:71:11 was injected to pressurize the interior to 16 kg/cm$^2$G. Thereafter, a 0.2% by weight aqueous solution of ammonium persulfate (10 ml) was injected to initiate polymerization.

As the reaction proceeded, the pressure dropped. When the pressure dropped to 15 kg/cm$^2$G, $I(CF_2)_4I$ (1.2 g) as a chain transfer agent was injected. When the pressure further dropped to 14 kg/cm$^2$G, a mixture of VdF, HFP and TFE in a molar ratio of 50:30:20 were injected to repressurize to 16 kg/cm$^2$G. With a repeating decrease and increase of pressure, the polymerization was continued while injecting the aqueous solution of ammonium sulfate (each 10 ml) every three hours.

When the total pressure drop reached 5 kg/cm$^2$G (about 5 hours from the initiation of polymerization), $ICH_2CF_2CF_2OCF=CF_2$ (1.8 g) was injected. Further, when the total pressure drop reached 43 kg/cm$^2$G (about 19 hours from the initiation of polymerization), the reaction vessel was cooled and the unreacted monomers were purged to give an aqueous emulsion with a solid content of 26.7% by weight.

To the emulsion, a 5% by weight aqueous solution of potassium alum was added to coagulate the product. The coagulated product was washed with water and dried to give an elastomeric copolymer (394 g). Mooney viscosity (100° C.), 83. Intrinsic viscosity [η], 0.53 dl/g (tetrahydrofuran, 35° C.). According to iodometry, the copolymer contained 0.12 % by mole of $ICH_2CF_2CF_2OCF=CF_2$.

Example 13

In the same manner as in Example 12 but using 5.4 g of $ICH_2CF_2CF_2OCF=CF_2$ and continuing the reaction for 31 hours, the polymerization was carried out to give an elastomeric copolymer (410 g). Mooney viscosity=48. [η]=0.34. Content of $ICH_2CF_2CF_2OCF=CF_2$=0.39% by mole.

Example 14

In the same manner as in Example 12 but using 9 g of $ICH_2CF_2CF_2OCF=CF_2$ and continuing the reaction for 34 hours, the polymerization was carried out to give an elastomeric copolymer (398 g). Mooney viscosity=43. [η]=0.31. Content of $ICH_2CF_2CF_2OCF=CF_2$=0.63% by mole.

Example 15

In the same manner as in Example 12 but using $ICH_2CF_2CF_2OCF(CF_3)CF_2OCF=CF_2$ (14.9 g) in place of $ICH_2CF_2CF_2OCF=CF_2$ and continuing the reaction for 9.5 hours, the polymerization was carried out to give an elastomeric copolymer (383 g). Mooney viscosity=47. Content of $ICH_2CF_2CF_2OCF(CF_3)CF_2OCF=CF_2$=0.74% by mole.

Example 16

In the same manner as in Example 11 but using as the initial monomeric mixture, a mixture of VdF and HFP in a molar ratio of 65:35 and as the additional monomeric mixture, a mixture of VdF and HFP in a molar ratio of 78:22, using 7.2 g of $ICH_2CF_2CF_2OCF=CF_2$ and proceeding the reaction for 25 hours and 45 minutes, the polymerization was carried out to give an elastomeric copolymer (345 g). Mooney viscosity=20. Content of $ICH_2CF_2CF_2OCF=CF_2$=0.52% by mole.

Comparative Example 2

In the same manner as in Example 11 but using no $ICH_2CF_2CF_2OCF=CF_2$ and continuing the reaction for 5 hours, the polymerization was carried out to give a copolymer (375 g). Mooney viscosity=87.

Comparative Example 3

In the same manner as in Example 11 but using no $ICH_2CF_2CF_2OCF=CF_2$ and 10 g of ammonium persulfate as a polymerization initiator and continuing the reaction for 4.1 hours, the polymerization was carried out to give a copolymer. Mooney viscosity =43.

The vulcanizing properties of the copolymers and physical properties of the cured copolymers were measured in the same manner as in Examples 6 to 10. The results are shown in Table 3.

TABLE 3

| Example No. | 11 | 12 | 13 | 14 | 15 | 16 | Comp. 2 | Comp. 3 |
|---|---|---|---|---|---|---|---|---|
| Copolymer (parts) | 100 | 100 | 100 | 100 | 100 | 100 | 100 | 100 |
| MT-carbon (parts) | 20 | 20 | 20 | 20 | 20 | 20 | 20 | 20 |
| Triallylisocyanurate (parts) | 4.0 | 4.0 | 4.0 | 4.0 | 4.0 | 4.0 | 4.0 | 4.0 |
| Perhexa-2,5B (parts) | 1.5 | 1.5 | 1.5 | 1.5 | 1.5 | 1.5 | 1.5 | 1.5 |
| $v_{min}$ (kg) | 0.04 | 0.17 | 0.05 | 0.03 | 0.05 | 0.01 | 0.19 | 0.05 |

TABLE 3-continued

| Example No. | 11 | 12 | 13 | 14 | 15 | 16 | Comp. 2 | Comp. 3 |
|---|---|---|---|---|---|---|---|---|
| $v$ (kg) | 2.98 | 4.45 | 4.80 | 4.70 | 3.05 | 3.87 | 0.30 | 0.21 |
| $T_{10}$ (min.) | 0.55 | 0.75 | 0.60 | 0.70 | 0.60 | 0.75 | — | — |
| $T_{90}$ (min.) | 3.30 | 2.05 | 1.90 | 2.80 | 3.00 | 4.70 | — | — |
| R (min.) | 2.75 | 1.30 | 1.30 | 2.10 | 2.40 | 3.95 | — | — |
| $M_{100}$ (kg/cm$^2$) | 92 | 35 | 65 | 91 | 89 | 49 | Foamed | |
| $T_B$ (kg/cm$^2$) | 151 | 198 | 210 | 204 | 160 | 168 | | |
| $E_B$ (%) | 140 | 290 | 210 | 180 | 180 | 190 | | |
| Hardness (JIS, Hs) | 72 | 69 | 71 | — | 71 | 69 | | |

Example 17

In a pressure resistant 100 ml glass ampoule equipped with a valve, $FCH_2CF_2CF_2OCF=CF_2$ (6.9 g), 1,1,2-trichloro-1,2,2-trifluoroethane (hereinafter referred to as "R-113") (10 ml) and a solution of 2,4,5-trichloro-perfluorohexanoylperoxide in R-113 (concentration, 0.7 g/ml) (0.5 ml) were charged and cooled by dry ice-methanol followed by replacement of the interior atmosphere with nitrogen gas. Then, vinylidene fluoride (6.8 g) was added to react at a 20±1° C. for 20 minutes with shaking. As the reaction proceeded, the pressure dropped from 6.3 kg/cm$^2$G to 5.5 kg/cm$^2$G. Thereafter, the unreacted monomers were purged, and the reaction mixture was dissolved in acetone and recovered from the ampoule. The solution was poured in pure water to precipitate the product, which was dried under reduced pressure until a constant weight was reached to give a copolymer (2.2 g).

According to $^1$H-NMR analysis, it was found that the copolymer contained vinylidene fluoride and $FCH_2CF_2CF_2OCF=CF_2$ in a molar ratio of 71.8:28.2. The glass transition temperature ($T_g$) of the copolymer was measured by a differential scanning calorimeter to be $-30°$ C. This $T_g$ suggested that the copolymer had good low temperature properties.

Example 18

In the same glass ampoule as used in Example 17, $F(CH_2CF_2CF_2O)_2CF=CF_2$ (10.8 g), R-113 (10 ml) and a solution of 2,4,5-trichloro-perfluorohexanoylperoxide in R-113 (concentration, 0.44 g/ml) (0.5 ml) were charged and cooled by dry ice-methanol followed by replacement of the interior atmosphere with nitrogen gas. Then, vinylidene fluoride (5.7 g) was added to react at 20±1° C. for 35 minutes with shaking. As the reaction proceeded, the pressure dropped from 9.8 kg/cm$^2$G to 6.8 kg/cm$^2$G. Thereafter, the unreacted monomers were purged, and the reaction mixture was dissolved in acetone and recovered from the ampoule. The solution was poured in pure water to precipitate the product, which was dried under reduced pressure until a constant weight was reached to give a copolymer (10.2 g).

According to 1H-NMR analysis, it was found that the copolymer contained vinylidene fluoride and $F(OCH_2CF_2CF_2O)_2CF=CF_2$ in a molar ratio of 72.8:27.2. $T_g$ of the copolymer was $-30.5°$ C.

Example 19

In the same manner as in Example 17 but using $F(OCH_2CF_2CF_2O)_3CF=CF_2$ (14.7 g) in place of $FCH_2CF_2CF_2OCF=CF_2$ and continuing the reaction for 23 minutes, the polymerization wa carried out to give a copolymer (16.2 g).

Molar ratio of vinylidene fluoride and $F(CH_2CF_2CF_2O)_3CF=CF_2=73.9:26.1$. $T_g=-42.0°$ C.

Example 20

In the same manner as in Example 17 but using tetrafluoroethylene (3.5 g) in place of vinylidene fluoride and continuing the reaction for one hour, the polymerization was carried out to give a copolymer (0.7 g). Any melting point was not observed since the copolymer was elastomeric.

$T_g=8.5°$ C.

Examples 21–25

In the same manner as in Example 17 but using monomers as shown in Table 4 and continuing the reaction for a period of time shown in Table 4, polymerization was carried out to give a copolymer, the molar content of the monomers and $T_g$ of which are shown in Table 4.

In Table 4, "VdF", "TFE", "FM" and "DLP" represent "vinylidene fluoride" "tetrafluoroethylene", $FCH_2CF_2CF_2OCF=CF_2$ and "a solution of 2,4,5-trichloro-perfluorohexayoylperoxide in R-113 (concentration, 0.7 g/ml)", respectively.

TABLE 4

| Example No. | 21 | 22 | 23 | 24 | 25 |
|---|---|---|---|---|---|
| Monomers | | | | | |
| VdF (g) | 0.6 | 1.8 | 5.5 | 0.5 | 1.4 |
| TFE (g) | 0.2 | 0.7 | 2.2 | 0.5 | 1.4 |
| FM (g) | 6.9 | 6.9 | 6.9 | 6.9 | 6.9 |
| Solvent | | | | | |
| R-113 (ml) | 10 | 10 | 10 | 10 | 10 |
| Initiator | | | | | |
| DLP (ml) | 0.5 | 0.5 | 0.5 | 0.5 | 0.5 |
| Temperature (°C.) | 20 | 20 | 20 | 20 | 20 |
| Time (minutes) | 30 | 20 | 15 | 30 | 20 |
| Yield (g) | 0.6 | 1.0 | 1.6 | 0.5 | 1.0 |
| Monomer content | | | | | |
| VdF (mole %) | 47.9 | 51.7 | 57.9 | 35.6 | 42.0 |
| TFE (mole %) | 3.6 | 9.4 | 15.4 | 27.9 | 25.9 |
| FM (mole %) | 48.5 | 38.9 | 26.7 | 36.5 | 32.1 |
| $T_g$ | −20 | −33 | −36.5 | −44.5 | −30 |

Example 26

In the same manner as in Example 17 but using ethylene (0.8 g) in place of vinylidene fluoride and continuing the reaction for 20 minutes, the polymerization was carried out to give a copolymer (0.8 g). Molar ratio of ethylene and $F(CH_2CF_2CF_2O)_3CF=CF_2=56.3:43.7$. $T_g=-11°$ C.

Example 27

In a 3 liter stainless steel autoclave equipped with a temperature controlling jacket, a stirrer and baffles, deionized deoxidized water (1.45) and ammonium tertiary phosphate (3 mg) were charged followed by the addition of ammonium perfluorooctanoate (9 mg). The autoclave was evacuated, injected by nitrogen gas and again evacuated. Evacuation and nitrogen injection were repeated three times. Then, injection and evacuation of tetrafluoroethylene were repeated twice. After the final evacuation, $FCH_2CF_2CF_2OCF=CF_2$ (1.2 g)

was added. Thereafter, the content was heated to 70° C. with stirring at 400 rpm. Tetrafluoroethylene was injected to pressurize the interior to 7.5 kg/cm$^2$G, and a solution of ammonium persulfate (4.0 mg) in water (50 ml) was injected together with tetrafluoroethylene to pressurize the interior to 8.0 kg/cm$^2$G. When the pressure started to drop, tetrafluoroethylene was continuously injected to maintain the pressure at 8.0 kg/cm$^2$G until 250 g of tetrafluoroethylene was consumed. Then, tetrafluoroethylene was purged and stirring was stopped to terminate the polymerization.

The resultant powdery product was recovered and charged in a mixer containing water and mixed and pulverized for one minute. The product was washed by changing water in the mixer for 5 minutes. Then, a fine powder of the product was dried at 150° C. for 14 hours.

From the dried powder, a film was molded and subjected to IR spectrum analysis to find that characteristic absorption peaks at 956 cm$^{-1}$ and 1,003 cm$^{-1}$ were present, which peaks are not found in IR spectrum of polytetrafluoroethylene.

From the ratio of the absorbances at 956 cm$^{-1}$ and 2,360 cm$^{-1}$, the content of $FCH_2CF_2CF_2OCF=CF_2$ in the resulting copolymer was calculated based on a calibration curve. The content of $FCH_2CF_2CF_2OCF=CF_2$ was 0.1% by mole.

Creep of the molded article of the polymer was 3.5% at 24° C.

Creep is measured as follows:

A powdery polymer (190 g) is charged in a cylindrical metal mold having a diameter of 50 mm, compress molded under a pressure of 300 kg/cm$^2$ for 5 minutes and removed from the mold. The molded polymeric article is sintered by heating it in a furnace up to 365° C. at a heating rate of 50° C./hr, kept at the same temperature for 5 hours and then cooled to a room temperature at a rate of 50° C./hr. The sintered article is cut to form a cylindrical rod having a diameter of 11.3 mm and a height of 10 mm while coinciding the axis direction of the rod with the compression direction. On the rod, a load of 140 kg/cm$^2$ is applied in the axis direction at a constant temperature of 24° C. Then, the height of the rod is measured after 10 seconds and 24 hours and creep (%) is calculated according to the following equation:

$$Creep = \frac{Height\ aft.\ 10\ sec. - Height\ aft.\ 24\ hrs.}{Original\ height} \times 100$$

Comparative Example 4

In the same manner as in Example 27 but using no $FCH_2CF_2CF_2OCF=CF_2$, the polymerization was carried out to give polytetrafluoroethylene, creep of which was 8.6% at 24° C.

Example 28

In the same autoclave, deionized deoxidized water (1.45 l), liquid paraffin (100 ml) and ammonium perfluorooctanoate (1.5 g) were charged, and injection and evacuation of nitrogen and tetrafluoroethylene were repeated in the same manner as in Example 27. After the final evacuation, $FCH_2CF_2CF_2OCF=CF_2$ (1.0 g) was added. Thereafter, the content was heated to 70° C. with stirring at 250 rpm. Tetrafluoroethylene was injected to pressurize the interior to 7.5 kg/cm$^2$G, and a solution of ammonium persulfate (11.3 mg) in water (50 ml) was injected together with tetrafluoroethylene to pressurize the interior to 8.0 kg/cm$^2$G. Tetrafluoroethylene was continuously injected at 70° C. to maintain the pressure at 8.0 kg/cm$^2$G until 730 g of tetrafluoroethylene was consumed. Then, tetrafluoroethylene was purged and stirring was stopped to terminate the polymerization.

The resultant dispersion was diluted with water and stirred together with ammonium carbonate to form a powdery product, which was dried at 130° C. for 14 hours.

The content of $FCH_2CF_2CF_2OCF=CF_2$ in the polymer was 0.04% by mole.

The dried powder was paste extruded under conditions as described in Japanese Patent Publication No. 28334/1984. The extruded article obtained in a stabilized stage was dried to remove the extruding aid and cut to form three sample rods each having a length of about 10 cm. The sample rods were subjected to a tensile test at a pulling rate of 20 cm/min., and tensile strength at break was measured and averaged for three samples. Extrusion pressure was 153 kg/cm$^2$, and tensile strength at break was 45 kg/cm$^2$.

Comparative Example 5

In the same manner as in Example 28 but using no $FCH_2CF_2CF_2OCF=CF_2$, the polymerization was carried out to give polytetrafluoroethylene. Extrusion pressure was 110 kg/cm$^2$, and tensile strength at break was 24 kg/cm$^2$.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. The fluorovinyl ether perfluoro(6,6-dihydro-3-oxa-1-hexene).

2. The fluorovinyl ether perfluoro(6,6,10,10-tetrahydro-3,7-dioxa-1-decene).

3. The fluorovinyl ether perfluoro(6,6,10,10,14,14-hexahydro-3,7,11-trioxa-1-tetradecene).

4. The fluorovinyl ether perfluoro(6,6-dihydro-6-iodo-3-oxa-1-hexene).

5. The fluorovinyl ether perfluoro(9,9-dihydro-9-iodo-5-trifluoromethyl-3,6-dioxa-1-nonene).

6. The fluorovinyl ether perfluoro(6-chloro-6,6-dihydro-3-oxa-1hexene).

* * * * *